US008375795B2

(12) United States Patent
Lingenberg et al.

(10) Patent No.: US 8,375,795 B2
(45) Date of Patent: Feb. 19, 2013

(54) NON-DESTRUCTIVE INSPECTION OF HIGH-PRESSURE LINES

(75) Inventors: Dieter Lingenberg, Hürth (DE); Reinhard Prause, St. Augustin (DE)

(73) Assignee: GE Sensing & Inspection Technologies GmbH (DE)

( * ) Notice: Subject to any disclaimer, the term of this patent is extended or adjusted under 35 U.S.C. 154(b) by 325 days.

(21) Appl. No.: 12/832,214

(22) Filed: Jul. 8, 2010

(65) Prior Publication Data

US 2011/0005321 A1 Jan. 13, 2011

(30) Foreign Application Priority Data

Jul. 9, 2009 (DE) .......................... 10 2009 027 598

(51) Int. Cl.
*G01N 29/04* (2006.01)

(52) U.S. Cl. ........................... 73/622; 73/114.45; 73/644

(58) Field of Classification Search .................... 73/622, 73/624, 627, 628, 649, 660, 114.45, 114.28, 73/114.51, 114.71, 114.78, 644
See application file for complete search history.

(56) References Cited

U.S. PATENT DOCUMENTS

| | | | | |
|---|---|---|---|---|
| 4,252,013 A | * | 2/1981 | Hyanova et al. ........... | 73/114.26 |
| 4,444,049 A | * | 4/1984 | Hitchcock .................. | 73/114.28 |
| 4,452,074 A | * | 6/1984 | Shelomentsev et al. ... | 73/114.28 |
| 4,656,870 A | * | 4/1987 | Ruthrof et al. .................. | 73/629 |
| 5,549,004 A | | 8/1996 | Nugent | |
| 5,811,671 A | * | 9/1998 | Seekircher et al. ........ | 73/114.45 |
| 5,834,629 A | * | 11/1998 | Hammarberg ............... | 73/35.08 |
| 6,164,137 A | | 12/2000 | Hancock et al. | |
| 6,859,763 B2 | * | 2/2005 | Van Polen ...................... | 702/189 |
| 2008/0236286 A1 | | 10/2008 | Lam et al. | |

FOREIGN PATENT DOCUMENTS

| | | |
|---|---|---|
| DE | 19747637 | 5/1999 |
| DE | 19931350 A1 | 12/2000 |
| DE | 10214678 | 10/2003 |
| EP | 2006675 A2 | 12/2008 |
| JP | 59-148864 | 8/1984 |
| WO | 0196855 A1 | 12/2001 |

OTHER PUBLICATIONS

J. and. H. Krautkramer, DIN EN 10228-3 1998-07 "Non-destructive testing of steel forgings—Part 3: Ultrasonic testing of ferritic or martensitic steel forgings" Werkstoffprüfung mit Ultraschall, sixth edition. (Concise explanation at pp. 2-3 of Specification).
DE102009027598.3 OA dated Jan. 22, 2010 with English Translation.
EP10169070.9 Search Report dated Mar. 19, 2012 with English Translation.
Ik_keun Park, et al., "Application of Ultrasonic Wave to Heat Exchanger Tubes Inspection," 17th World Conference on Nondestructive Testing, Oct. 25-28, 2008, Shanghai, China.

* cited by examiner

*Primary Examiner* — J M Saint Surin
(74) *Attorney, Agent, or Firm* — Cantor Colburn LLP

(57) ABSTRACT

The invention relates to a method for the non-destructive ultrasound inspection of a high-pressure line as a testing piece by means of the pulse-echo method, where the high-pressure line is conveyed to a near-field range of at least one ultrasonic transducer and an ultrasonic pulse is emitted with a perpendicular sound incidence on the high-pressure line in such a way that the high-pressure line is completely captured in its cross section by the near-field sound emission caused by the ultrasonic transducer, and the reflected ultrasonic pulse(s) is/are received by the ultrasonic transducer and/or, optionally, further ultrasonic transducers, the associated echo delay times are recorded and, optionally, evaluated.

9 Claims, 2 Drawing Sheets

NON-DESTRUCTIVE INSPECTION OF HIGH-PRESSURE LINES

TECHNICAL FIELD

The invention relates to a method for inspecting a high-pressure line as a test piece.

BACKGROUND

It is known to test high-pressure lines, in particular also metal high-pressure lines for a fuel injection system, for manufacturing or material flaws by means of pressurization. In the process, the pipes are usually pressurized with a pressure above the actual operating pressure, under provisions regarding pressure increase and retention time of the testing pressure, in order to carry out a reject test. As is known, this test is deficient because it does not enable any information about the inner structure of the pipes. Structural flaws in the inner structure of the pipes, which may not lead to an acute failure of the pipes, but which nevertheless constitute a risk of future failure, are not recognized in this way. Attempts for inspecting the pipes in a non-destructive and volume-oriented manner made so far failed because of the costs, with respect to the usual radiography-based inspections.

On the other hand, and in particular where ultrasound was concerned, the prejudice prevailed with regard to these high-pressure lines, which, compared to the usual test specimens for ultrasonic testing, generally had small dimensions, that ultrasound was not suitable, due to the comparatively large dimensions of the sound transducers, and could not be coupled in in a reproducible manner for the purpose of an inspection. In addition, there is the problem, as a rule, that these pipes are not configured in a straight line, so that the usual approaches such as those that are customary in the inspection of gas or oil pipelines, and which provide, for example, an irradiation angled in circumferential direction of the tube in order to cause a sound propagation in the circumferential direction, fail in the inspection of high-pressure lines because the required angle for the defined angled emission of the ultrasonic transducer into the test piece cannot be maintained, or at least not reproducibly.

BRIEF SUMMARY

The inventors must be credited with having recognized that high-pressure lines, in particular for fuel injection systems, can be effectively inspected by means of ultrasound using the pulse-echo method, despite the above-described prejudices. In view of the above-described prior art, the invention provides a more reliable method for material testing of high-pressure lines, in particular of fuel injection lines.

It is provided, according to the invention, that, in the method for the non-destructive ultrasound inspection of the high-pressure line as a testing piece by means of the pulse-echo method, the high-pressure line is conveyed to a near-field range of at least one ultrasonic transducer and an ultrasonic pulse is emitted with a perpendicular sound incidence on the high-pressure line in such a way that the high-pressure line is completely captured in its cross section by the near-field sound emission caused by the ultrasonic transducer. The invention further provides receiving the reflected ultrasonic pulse(s) by the ultrasonic transducers and/or, optionally, further ultrasonic transducers, recording and, optionally, evaluating the echo delay times. The term "high-pressure line" within the sense of the invention is to be interpreted broadly and also includes, for example, lines with a minimal internal diameter, as compared with the external diameter, and also those with an internal diameter reduced to zero. Preferably, metal fuel lines for internal combustion engine with a fuel injection system are concerned.

In the prior art, ultrasound testing, in particular the pulse-echo method, is a suitable testing method for finding internal and external flaws in sound-conducting materials (to which most metals belong). Like all testing methods, ultrasound inspection is also standardized and is carried out in accordance with guidelines, such as according to DIN EN 10228-3 1998-07 Non-destructive testing of steel forgings—Part 3: Ultrasonic testing of ferritic or martensitic steel forgings, which is hereby incorporated by reference. Suitable testing devices and methods are known for the non-destructive testing of a test piece by means of ultrasound. General reference is made to the textbook by J. and H. Krautkrämer, Werkstoffprüfung mit Ultraschall, sixth edition.

This method is generally based on the reflection of sound on boundary surfaces. The sound source most frequently used is a test probe with at least one ultrasonic transducer with an emission which is in each case in the frequency range of 10 kHz to 100 MHz, typically 10 MHz. In the case of the pulse-echo method, the ultrasonic probe does not emit a continuous radiation, but very short sound pulses with a duration of 1 μs and less. The pulse emanating from the transmitter passes through the test piece to be inspected, in this case the high-pressure line, with the respective speed of sound, and is almost completely reflected at the existing boundary surfaces. The sound transducer is mostly not only able to transmit pulses, but also to convert incoming pulses into electrical measuring signals; it thus also works as a receiver. The time required by the sound pulse to travel from the transmitter through the work piece and back again is measured with an oscilloscope or a computer unit. Given a known speed of sound c in the material, the thickness of a sample, for example, can thus be checked. A couplant, such as a gel, water or oil, is introduced in the region between the high-pressure line and the ultrasonic transducer for coupling them. In the case of a relative movement between the transducer and the test piece, the test piece in one embodiment is often immersed in a suitable liquid (immersion technique) or wetted in a defined manner for the purpose of transmitting the sound signal.

Changes in the acoustic properties on boundary surfaces, i.e. at the external wall surfaces delimiting the test piece, but also at the internal boundary surfaces, i.e. internal flaws such as piping (cavity), a pocket, a lamination, a tear or another interruption in the structure within the high-pressure line to be inspected reflect the sound pulse and transmit it back to the transducer in the test probe, which acts both as a transmitter as well as a receiver. The time that has passed between the transmission and the receipt makes it possible to calculate the distance. Using the measured difference in time, a signal image is generated and made visible on a monitor or oscilloscope. Using this image of the delay time behavior, the position can be determined and the size of the flaw (which in the technical jargon is called discontinuity) can be estimated, if necessary, by comparison with a substitute reflector (flat bottom hole (circular disc reflector), groove, transverse hole). Generally, discontinuities with a size of approx. 0.6 mm can be detected, down to 0.1 mm or even smaller in the case of special methods. In the case of automatic testing plants, the information is stored, put in relation to the test piece, and documented in various manners immediately or later.

The method according to the invention is characterized in that the emission is substantially perpendicular, i.e. the emission direction of the transducer is substantially perpendicular to a plane spanned by a radial and the axial direction (longitudinal direction) of the tubular line. According to the invention, the test specimen or test piece, in this case the high-pressure line, is conveyed to the near field of the ultrasonic transducer. The near field is the emission region closest to the transducer extending up to the so-called focus. The focus (plane, line or point focus) is the area of the ultrasonic radiation pattern of a transducer with the smallest diameter and the largest lateral resolution. The focal zone, as a natural "beam waist", lies in the transitional area between the inhomogeneous near field and the divergent far field with its homogeneous, plane sound wave fronts. What is essential for the invention is that the ultrasound of this near field is suitable for completely capturing the high-pressure line in its cross section. Due to diffraction effects and wave separation in different types of wave propagation (longitudinal or transversal), the radiation distribution in the test piece may expand and a complete capture of the cross section of the line can be accomplished, even though such a width would not be provided by the radiation lobe of the emission pattern by itself, i.e. without the line having been introduced. Preferably, however, it is ensured that near-field emission of the transducer, which is independent from the test specimen, can be brought into complete coincidence with the cross section of the test specimen by the transducer, or the line, being dimensioned such that the cross section of the conductor can fall completely within the theoretically determined, test-specimen-free near-field range. A reliable detection is thus achieved.

Preferably, a piezo crystal oscillator is used as the ultrasonic transducer in the method according to the invention, the transverse dimension of which substantially corresponds to the external diameter of the high-pressure line.

Surprisingly, it was found that the near-field sound emission described above, which completely captures the test piece in its cross section, is suitable for being able to recognize flaws in the material and/or the surface of the high-pressure line, for example abrupt changes of wall thickness, pockets (piping), foreign bodies in the pipe wall as well as surface damage on the external and internal wall of the pipe, and in particular, tears oriented in the longitudinal direction. It was found that the usual methods for flaw evaluation can be used.

Preferably, an amplitude evaluation of the ultrasonic echo signals is carried out during evaluation. So-called gates and monitor thresholds are set, for example. The monitor thresholds for the surface and back-face echoes evaluate the amplitude with negative logic (anticoincidence), that is, if the amplitude drops below the set monitor threshold due to a lowering of the echo, then an output signal is set. The flaw echo, however, is an additional amplitude which the display evaluates with positive logic (coincidence). If the flaw amplitude exceeds the set monitor threshold, then an output signal is set. Generally, the gates are determined by determination on one or more test specimens with or without reference flaws.

Furthermore, it was found that the method according to the invention is particularly efficient and reliable with regard to flaw detection if the echo delay time range until the echo or multiple echo of the external wall (back face) facing away from the ultrasonic transducer is preferably subjected to an amplitude evaluation between the echo on the internal wall closest to the ultrasonic transducer and the third echo on the external wall facing away from the ultrasonic transducer.

Preferably, a back-face echo and/or a multiple back-face echo is subjected to an amplitude evaluation with regard to anticoincidence in the evaluation. It was found that the "loss" or reduction of the amplitude concerning the back-face echoes to be expected makes it possible to reliably detect flaws in the area of the internal pipe surface.

Conveying the high-pressure line in accordance with the invention can comprise a translational and/or rotating movement of the high-pressure line. The procedure is generally known to the person skilled in the art. For example, conveying and advancing can be carried out intermittently between test cycles, in which ultrasound irradiation takes place in different sections and/or under different angles, possibly by several ultrasonic transducers disposed offset in the axial and/or radial direction, for example by 8, 12, 16, 24 ultrasonic transducers, in order to completely capture the high-pressure line. In another embodiment, the problem of the complete inspection of the high-pressure line is solved by a transducer rotating in the circumferential direction about the high-pressure line.

In the methods for non-destructive ultrasound inspection of a test piece, it is of utmost importance to provide for good coupling of the ultrasonic transducer and monitor it in order to achieve and maintain a high quality of material testing. Coupling can take place by means of a water gap or water chamber, by the immersion technique or squirter technique. Coupling by means of a rotating water jacket has proven the most favorable approach. An arrangement therefor is known from DE19931350A1, which is hereby incorporated by reference.

According to the invention, the external diameter of the line is in the range of the transverse dimension of the piezo effect-based ultrasonic transducers typically used. By multiple tests, the inventors were able to find that high-pressure lines with an external diameter of 10 mm or less are particularly suitable for this type of inspection, preferably of 8 mm or less, more preferably of 6 mm or less.

The inventors found, through comprehensive tests, that the method according to the invention is particularly suitable for the following internal diameters of 5 mm or less, preferably of 3 mm or less, more preferably of 2 mm or less, still more preferably of 1.5 mm or less.

In another embodiment, means can be provided for the locally selective attenuation of the ultrasonic emission in the sound penetration area between the test piece and the transducer. For example, a sound-attenuating body, for example of a porous material, such as cork, with a transverse dimension smaller compared with that of the transducer is provided in the center of the transducer in order to attenuate the sound in the central area of the sonic cone.

The invention further relates to an arrangement including a device for carrying out the method in any one of the above-described embodiments and a high-pressure line as a test piece, wherein the device comprises the following: at least one ultrasonic transducer, means for conveying the high-pressure line into the near-field range of the ultrasonic transducer, wherein the ultrasonic transducer is disposed such that it emits an ultrasonic pulse with a perpendicular sound incidence onto the high-pressure line in such a way that the high-pressure line is completely captured in its cross section by the near-field sound emission caused by the ultrasonic transducer, and that the reflected ultrasonic pulse(s) is/are received by the ultrasonic transducer and/or, optionally, further ultrasonic transducers, and means for recording and, optionally, evaluating the associated echo delay times, for example with a display for representing the delay time behavior. The evaluation means provide, for example, the logical evaluation of the echo amplitudes with regard to coincidence or anticoincidence.

BRIEF DESCRIPTION OF THE DRAWINGS

The invention as well as the technical environment are explained in more detail with reference to the figures. It must be remarked that the Figures depict particularly preferred embodiments of the invention, but that the latter is not limited thereto. The Figures schematically show.

DETAILED DESCRIPTION

Figure 1:
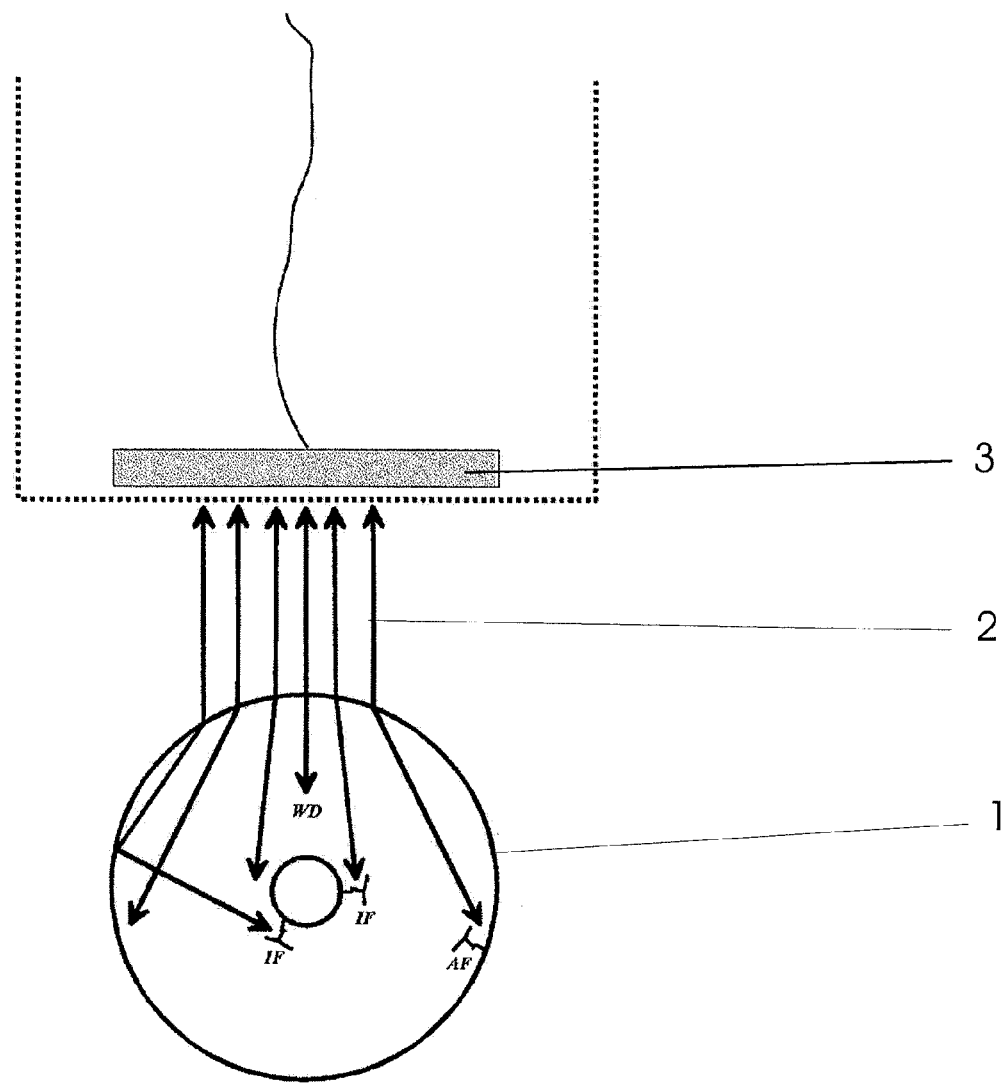
FIG. 1 shows a cross section of an arrangement according to the invention for carrying out the above-described method.

FIG. 1 shows a cross section of an arrangement according to the invention for carrying out the above-described method. The ultrasonic transducer 3, in this case a piezo crystal transducer, has a transverse dimension which substantially corresponds to the external diameter of the high-pressure line 1 to be inspected. The sound propagation of the ultrasound 2 is schematically represented by double arrows. What is essential for the invention is that the high-pressure line 1 is disposed in the ultrasonic near-field range 2 of the ultrasonic transducer 3, and that this orientation relative to the transducer 3 is maintained during the further transport of the high-pressure line 1 in a direction perpendicular to the paper plane of the Figure. This is accomplished, for example, by sleeve-shaped guides, which are not shown. As is apparent from the schematic structure, the transducer 3 is aligned such that the primary propagation direction of the sound 3, which substantially matches the direction of the double arrow WD, perpendicularly hits a plane spanned by the radius and the axial or longitudinal direction, respectively, of the line 1. Preferably, the primary orientation perpendicularly crosses the central longitudinal axis of the line 1 in the inspected portion concerned.

Figure 2:
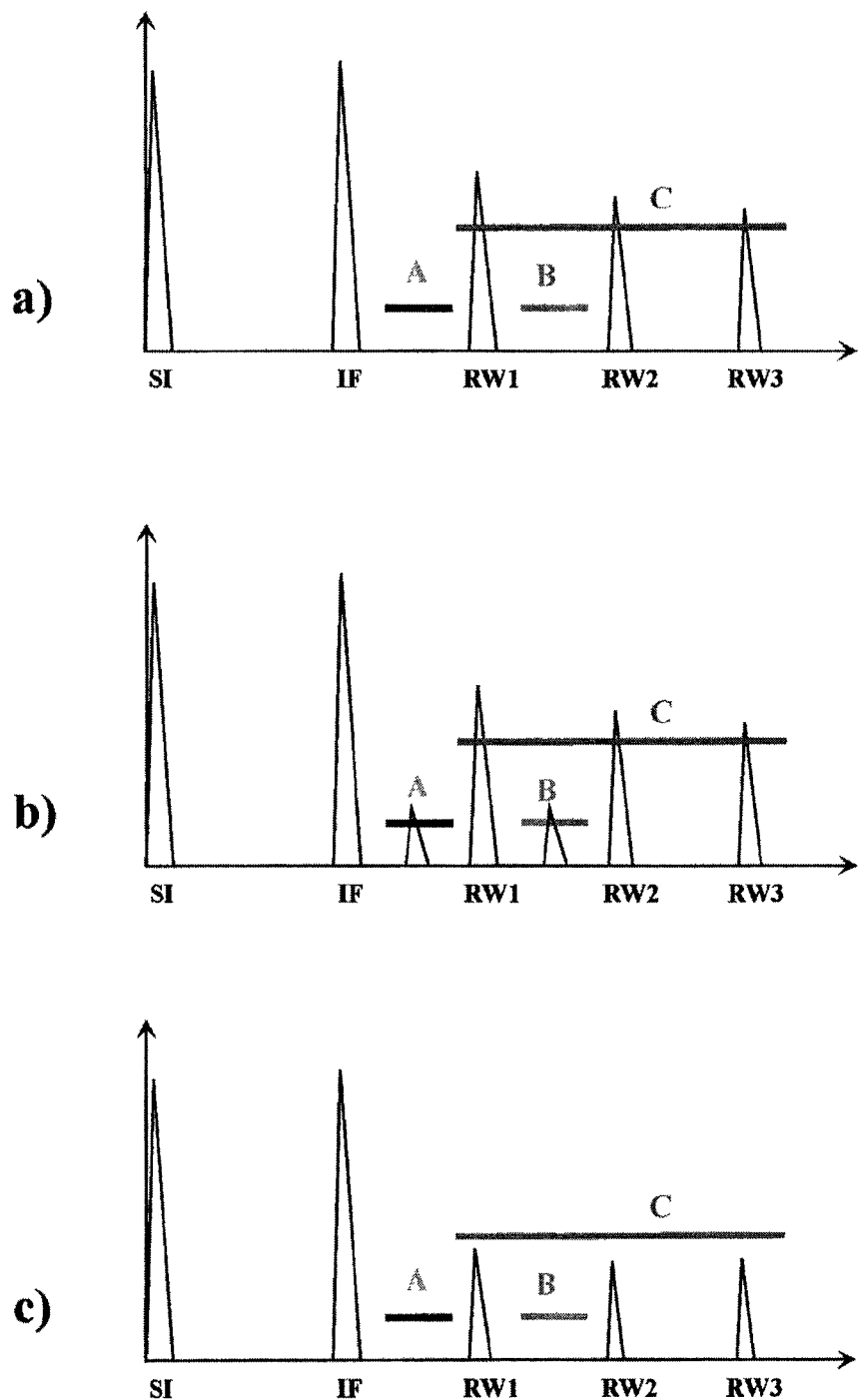
FIGS. 2a-2c represent the delay time behavior and the amplitudes of echoes schematically.

The sound propagation of the near field of the transducer 3, if applicable, due to diffraction effects and wave transformation in the material of the test piece, is such that the test piece 1 is completely captured. As is apparent from FIGS. 2a-2c, which represent the delay time behavior and the amplitudes of the echoes schematically, typical echoes resulting from the dimensioning of the line 1, such as back-face echoes RW1 to RW3 and, possibly, flaw echoes occur. While SI designates the transmission echo, IF is an internal flaw which can typically be easily identified as an echo in the delay time representation. The gates A (gate between the internal wall echo and the first back-face echo RW1) and B (gate between the first and the second back-face echo) serve for detecting lateral flaws, i.e. flaws AF (see FIG. 1) that lie to the side of the primary emission direction in the material of the test piece 1, and are thus being evaluated logically by an evaluation unit, which is not shown, in such a way that they cause a detection signal when a threshold is exceeded (coincidence).

The gate C acquires the time range of the back-face echo approximately from the first until the third back-face echo RW1 to RW3. Its amplitude reduction or loss is logically evaluated with regard to anticoincidence by the evaluation unit, which is not shown, and the detection signal generated thereby indicates a flawed internal pipe diameter, i.e. a flaw in the area of the internal wall of the line 1.

The invention claimed is:

1. A method for non-destructive ultrasound inspection of a high-pressure line as a testing piece by means of a pulse-echo method, wherein the high-pressure line is conveyed to a near-field range of at least one ultrasonic transducer and an ultrasonic pulse is emitted with a perpendicular sound incidence on the high-pressure line in such a way that the high-pressure line is completely captured in its cross section by the near-field sound emission caused by the ultrasonic transducer, and reflected ultrasonic pulse(s) is/are received by the ultrasonic transducer and/or, optionally, further ultrasonic transducers, the associated echo delay times are recorded and, optionally, evaluated, wherein, during an evaluation, an echo delay time range until an echo or multiple echo at an external wall of the high-pressure line facing away from the ultrasonic transducer, preferably between an echo on an internal wall closest to the ultrasonic transducer and a third echo on the external wall facing away from the ultrasonic transducer, is subjected to an amplitude evaluation.

2. The method for the non-destructive ultrasound inspection according to claim 1, wherein the high-pressure line is conveyed in such a way that its cross section lies within the near-field range of the ultrasonic transducer.

3. The method for the non-destructive ultrasound inspection according to claim 1, wherein the ultrasonic transducer is a piezo oscillator, a transverse dimension of which substantially corresponds to an external diameter of the high-pressure line.

4. The method for the non-destructive ultrasound inspection according to claim 1, wherein a rotating water jacket is used for acoustic coupling between the at least one ultrasonic transducer and the high-pressure line.

5. The method for the non-destructive ultrasound inspection according to claim 1, wherein, during the evaluation, a back-face echo and/or a multiple back-face echo is subjected to an amplitude evaluation with regard to anticoincidence.

6. The method for the non-destructive ultrasound inspection according to claim 1, wherein the high-pressure line has an external diameter of 10 mm or less.

7. The method for the non-destructive ultrasound inspection according to claim 6, wherein the high-pressure line has an internal diameter of 5 mm or less.

8. The method for the non-destructive ultrasound inspection according to claim 1, further comprising a plurality of ultrasonic transducers disposed offset in a circumferential direction and/or an axial direction.

9. An arrangement comprising a device for carrying out the method according to claim 1 and a high-pressure line as a test piece, wherein the device comprises: at least one ultrasonic transducer, means for conveying the high-pressure line into a near-field range of the ultrasonic transducer, wherein the ultrasonic transducer is disposed such that it emits an ultrasonic pulse with a perpendicular sound incidence onto the high-pressure line in such a way that the high-pressure line is completely captured in its cross section by the near-field sound emission caused by the ultrasonic transducer, and that reflected ultrasonic pulse(s) is/are received by the ultrasonic transducer and/or, optionally, further ultrasonic transducers, and means for recording and, optionally, evaluating the associated echo delay times.

* * * * *